United States Patent [19]

Kraus

[11] Patent Number: 4,545,935
[45] Date of Patent: Oct. 8, 1985

[54] AMIDOALKYLATION REACTIONS OF ANILINES

[75] Inventor: George A. Kraus, Ames, Iowa

[73] Assignee: Iowa State University Research Foundation, Inc., Ames, Iowa

[21] Appl. No.: 531,213

[22] Filed: Sep. 12, 1983

[51] Int. Cl.[4] .................. A61K 31/55; C07D 471/04; C07D 487/04
[52] U.S. Cl. .................. 260/245.7; 260/239.3 T; 260/244.4
[58] Field of Search .................. 260/239.3 T, 245.7, 260/244.4

[56] References Cited

U.S. PATENT DOCUMENTS

| | | | |
|---|---|---|---|
| 3,374,264 | 3/1968 | Liskokovic et al. | 260/239 BD |
| 3,384,635 | 5/1968 | Carabateas | 260/239 BD |
| 3,419,569 | 12/1968 | Renner | 424/274 |
| 3,481,921 | 12/1969 | Field et al. | 260/239 BD |
| 3,573,322 | 3/1971 | Hester | 424/274 |
| 3,651,083 | 3/1972 | Hester | 260/245.7 |
| 3,652,588 | 3/1972 | Hester | 424/274 |
| 3,732,212 | 5/1973 | Carabateas | 260/245.7 |
| 3,734,919 | 5/1973 | Hester | 260/245.7 |
| 3,763,183 | 10/1973 | Carabateas | 260/245.5 |
| 3,824,230 | 7/1974 | Hester | 260/245.7 |
| 3,828,039 | 8/1974 | Nakanishi et al. | 424/275 |
| 3,833,591 | 9/1974 | McManus | 424/263 |
| 3,839,357 | 10/1974 | Hester | 424/274 |
| 3,846,443 | 11/1974 | Moffett | 424/273 |
| 3,867,374 | 2/1975 | Reynolds et al. | 260/239.3 T |
| 3,910,946 | 10/1975 | Gall | 260/245.5 |
| 3,914,250 | 10/1975 | Kim | 260/245.7 |
| 3,933,794 | 1/1976 | Hester et al. | 260/239 BD |
| 3,980,797 | 9/1976 | Jonas et al. | 260/245.7 |
| 3,984,562 | 10/1976 | Wright | 260/245.7 |
| 3,998,842 | 12/1976 | White et al. | 424/274 |
| 4,169,150 | 9/1979 | Hara et al. | 424/274 |
| 4,186,199 | 1/1980 | Glamkowski et al. | 424/232 |
| 4,264,499 | 4/1981 | Hirai et al. | 260/245.5 |
| 4,362,666 | 12/1982 | Wasley | 260/245.7 |

OTHER PUBLICATIONS

Seto et al. Chem. Abstracts, vol. 89, Abstract No. 146944v, (1978).
Kraus, Chem. Abstracts, vol. 95, Abstract No. 7550z, (1981).
Hoover et al., *Journal of Organic Chemistry*, vol. 28, pp. 1825-1830, (1963).

*Primary Examiner*—Alton D. Rollins
*Attorney, Agent, or Firm*—Zarley, McKee, Thomte, Voorhees & Sease

[57] ABSTRACT

Benzodiazepines having associated carbonyl lactam ring structure are synthesized from N-2-bromoethyl-5-alkoxy-2-pyrrolidinone and analine compounds, in the first ever such direct single step synthesis. The produced compounds are known biological active compounds having anti-anxiety activity similar to Valium.

10 Claims, No Drawings

AMIDOALKYLATION REACTIONS OF ANILINES

BACKGROUND OF THE INVENTION

Certain benzodiazepine compounds are known to have biological activity as anxiety reducing agents. For example, perhaps one of the most famous of such compounds is diazepam sold under the trademark Valium. However, heretofore, there has been no direct, single step synthesis of high yield for preparing such compounds. This has inhibited the research in the area of investigative effort for other biologically active compounds.

SUMMARY OF THE INVENTION

The primary objective of the present invention is to prepare benzodiazepine derivatives having a carbonyl lactam moiety, by a single step, direct synthesis. The compounds are biologically active and exhibit anti-anxiety behavior, similar to that of Valium.

Another objective of the present invention is to provide a simple, direct single step synthesis of the previously described compounds in a manner which is economical and suitable for large scale industrial reactions in high yield.

Another objective of the present invention is to synthesize benzodiazepine compounds having an associated carbonyl lactam group.

The method and manner of accomplishing each of the above objectives, as well as others, will become apparent from the detailed description of the invention which follows.

DETAILED DESCRIPTION OF THE INVENTION

In accordance with this invention, benzodiazepines of the following formula are prepared:

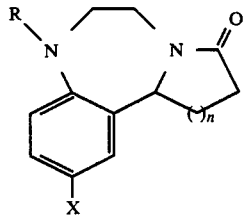

"R" represents a $C_1$ to $C_{12}$ alkyl group, preferably a $C_1$ to $C_4$ alkyl group. "X" represents hydrogen, chloro or a simple alkoxy group, such as methoxy or ethoxy. "n" can suitably be one, two or three, preferably one.

Quite surprisingly, the compounds of this invention, although fairly complex in structure, can be prepared by a simple, direct, single step synthesis. The compounds are prepared by reacting an N-alkyl aniline of the formula

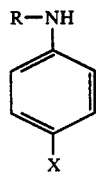

wherein "R" and "X" are as previously defined, with an N-2-bromoethyl-5-alkoxy-2-pyrrolidinone of the formula

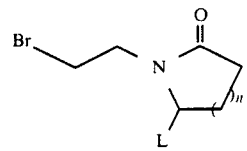

wherein "L" represents a leaving group. Any suitable leaving group can be employed, but alkoxy groups are preferred with methoxy and ethoxy being most preferred. Other suitable leaving groups are S-phenyl and S-alkyl.

The reaction can be conducted without any solvent present and is ideally conducted at temperatures of from about 50° C. to about 80° C., preferably from about 60° C. to about 75° C.

The reaction is an unexpectedly facile synthesis of the benzodiazepine skeleton. While not wishing to be bound by any theory, it is believed that the reaction is catalyzed by an intermediate amine hydrobromide produced in situ. The reaction can be thought of as an intramolecular amidoalkylation.

The reaction is further illustrated, but not limited by the following examples.

EXAMPLES

Materials were obtained from commercial suppliers and were used without purification. Dichloromethane was distilled from $P_2O_5$. Melting points were determined on a Fisher-Jones melting point apparatus. Infrared spectra were determined on a Befkman IR-4250 spectrometer. Nuclear magnetic resonance spectra were determined on a Varian EM360 60 MHz instrument. Carbon-13 NMR spectra were determined on a JOEL FX-900 Fourier transform instrument. Both proton and carbon chemical shifts are expressed in parts per million downfield from internal tetramethylsilane. High-resolution mass spectra were recorded on an AEI MS-902 high resolution mass spectrometer. These quantitative and qualitative tests confirmed the presence of the reported compounds.

One equivalent of the lactam

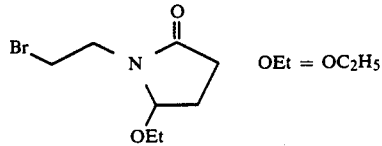

and two equivalents of the aniline of the general formula

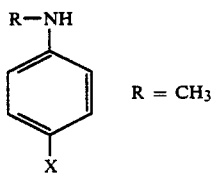

were heated at 70° C. without solvent. For the preparation of the compound (X=H), (X=Cl) and (X=OCH$_3$), the reactants were heated, respectively, for 12, 14 and two hours. The crude product was purified by chromatography on the silica gel, and analysis in accordance with the above described techniques was conducted. The analysis for each of these three products revealed the following:

(X=H): m.p. 88.5°–89.5° C. NMR (CDCl$_3$) 2.15–2.55 (m, 4H), 2.85 (s, 3H), 2.75–3.2 (m, 2H), 3.3–3.65 (m, 2H), 4.90 (bt, J–6 Hz, 1H), 6.75–7.30 (m, 4H); IR (nujol) 1675 cm$^{-1}$; mass spectrum, m/e calcd for C$_{13}$H$_{16}$N$_2$O (m+) 216.12627, found 216.12619.

(X=Cl): m.p. 81°–83° C. NMR (CDCl$_3$) 2.15–2.50 (m, 4H), 2,85 (s, 3H), 2.6–3.23 (m, 2H), 3.23–3.60 (m, 2H), 4.5–4.9 (m, 1H), 6.83 (dd, J=2, 5 Hz, 1H), 7.0–7.3 (m, 2H); CMR (CDCl$_3$) 24.71; 30.50, 39.60, 41.68, 54.63, 58.98, 119.07, 125.83, 126.48, 128.24, 131.95, 149.92, 173.31; mass spectrum, m/e calc for Cl4H18N2o2 (m+) 246.13683, found 246.13637.

(X=OCH$_3$): NMR (CDCl$_3$) 2.1–2.5 (m, 4H), 3.4–4.5 (m, 4H), 3.75 (S, 3H), 4.7–5.0 (m, 1H), 6.6–7.1 (m, 3H). IR (film) 1695, 1495, 1205, 1060, 1030. m/e calcd for C$_{13}$H$_{15}$O$_3$N: 233.10520; measured 233.10577.

The invention is a highly effective and efficient direct single step synthesis.

What is claimed is:

1. A process of preparing Benzodiazepines of the formula:

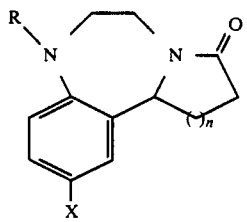

wherein "R" and "X" are as hereinafter defined and "n" is a whole integer and is 1, 2 or 3, by a direct single step synthesis reaction of an N-alkylaniline of the formula:

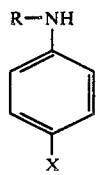

wherein "R"0 equals C$_1$ to C$_{12}$ alkyl group, and X equals hydrogen, Cl, or alkoxy, with an alkoxy lactam of the formula:

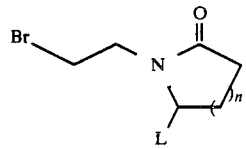

wherein "L" is a leaving group.

2. The process of claim 1 wherein L is a leaving group selected from the group consisting of alkoxy, S-phenyl and S-alkyl.
3. The process of claim 2 wherein "L" is ethoxy.
4. The process of claim 1 wherein "n"=1.
5. The process of claim 1 wherein "R" is C$_1$ to C$_4$.
6. The process of claim 1 wherein "X" is hydrogen.
7. The process of claim 1 wherein "X" is chlorine.
8. The process of claim 1 wherein the reaction is conducted at a temperature of about 50° C. to about 80° C.
9. The process of claim 8 wherein the reaction is conducted at a temperature of from about 60° C. to about 75° C.
10. A compound of the formula:

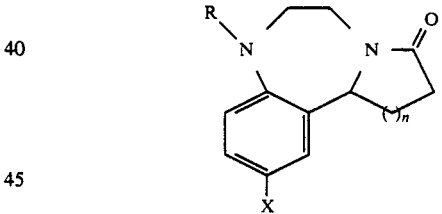

wherein "R" is a C$_1$ to C$_{12}$ alkyl group, "X" is hydrogen, chloro or alkoxy, and n is 1, 2 or 3.

* * * * *